(12) United States Patent
Nguyen-Kim et al.

(10) Patent No.: US 7,459,148 B2
(45) Date of Patent: Dec. 2, 2008

(54) COSMETIC AGENT CONTAINING AT LEAST ONE COPOLYMER HAVING N-VINYLLACTAM UNITS

(75) Inventors: Son Nguyen-Kim, Hemsbach (DE); Peter Hoessel, Schifferstadt (DE); Walter Schunter, Freinsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 55 days.

(21) Appl. No.: 10/497,164

(22) PCT Filed: Dec. 10, 2002

(86) PCT No.: PCT/EP02/14015

§ 371 (c)(1),
(2), (4) Date: Jun. 8, 2004

(87) PCT Pub. No.: WO03/053381

PCT Pub. Date: Jul. 3, 2003

(65) Prior Publication Data

US 2005/0053566 A1    Mar. 10, 2005

(30) Foreign Application Priority Data

Dec. 11, 2001    (DE) ............... 101 60 720

(51) Int. Cl.
- A61Q 5/00 (2006.01)
- A61Q 5/06 (2006.01)
- A61Q 7/00 (2006.01)
- A61K 8/73 (2006.01)

(52) U.S. Cl. ............ 424/70.11; 424/70.15; 424/70.17

(58) Field of Classification Search ........... 424/70.11, 424/70.15–70.17

See application file for complete search history.

(56) References Cited

U.S. PATENT DOCUMENTS

| | | | | |
|---|---|---|---|---|
| 4,272,611 A * | 6/1981 | Vyvial et al. | ............ | 430/306 |
| 4,380,600 A * | 4/1983 | Hosoda et al. | ............ | 524/458 |
| 4,904,408 A * | 2/1990 | Kud et al. | ............ | 510/360 |
| 5,086,142 A * | 2/1992 | Fock et al. | ............ | 526/318 |
| 5,196,188 A | 3/1993 | Potthoff-Karl et al. | | |
| 5,608,021 A | 3/1997 | Uchiyama et al. | | |
| 5,632,977 A | 5/1997 | Chandran et al. | | |
| 5,635,554 A * | 6/1997 | Boeckh et al. | ............ | 524/377 |
| 5,686,067 A | 11/1997 | Shih et al. | | |
| 5,739,195 A | 4/1998 | Kroker et al. | | |
| 6,048,945 A * | 4/2000 | Denzinger et al. | ............ | 525/403 |
| 6,139,827 A * | 10/2000 | Cohen et al. | ............ | 424/70.16 |
| 6,239,227 B1 * | 5/2001 | Schoonbrood et al. | ............ | 525/283 |
| 6,262,176 B1 * | 7/2001 | Kim et al. | ............ | 525/127 |
| 6,447,696 B1 * | 9/2002 | Takagi et al. | ............ | 252/180 |
| 2003/0147929 A1 * | 8/2003 | Kim et al. | ............ | 424/401 |
| 2005/0175572 A1 | 8/2005 | Nguyen-Kim et al. | | |

FOREIGN PATENT DOCUMENTS

| | | |
|---|---|---|
| DE | 29 24 663 | 12/1979 |
| DE | 37 16 380 | 11/1987 |
| DE | 44 09 903 | 9/1995 |
| DE | 44 34 986 | 4/1996 |
| DE | 100 08 263 | 8/2001 |
| DE | 100 41 211 | 3/2002 |
| EP | 0 257 444 | 3/1988 |
| EP | 417901 | 3/1991 |
| EP | 0 480 280 | 4/1992 |
| EP | 1 002 811 | 5/2000 |
| EP | 1 110 536 | 6/2001 |
| JP | 5-5721 | 1/1993 |
| JP | 5-255057 | 10/1993 |
| JP | 6-184251 | 7/1994 |
| JP | 2000-178323 | 6/2000 |
| WO | WO 93/18073 | 9/1993 |
| WO | WO 95/15986 | 6/1995 |
| WO | WO 96/10593 | 4/1996 |
| WO | WO 96/20691 | 7/1996 |
| WO | 96/34903 | 11/1996 |
| WO | 99/04750 | 2/1999 |
| WO | WO 00/14132 | 3/2000 |
| WO | 00/68282 | 11/2000 |
| WO | WO 01/62809 | 8/2001 |
| WO | WO 0162809 A1 * | 8/2001 |

\* cited by examiner

*Primary Examiner*—Sreeni Padmanabhan
*Assistant Examiner*—Renee Claytor
(74) *Attorney, Agent, or Firm*—Oblon, Spivak, McClelland, Maier & Neustadt, P.C.

(57) ABSTRACT

The present invention relates to a cosmetic composition which comprises at least one water-soluble or water-dispersible copolymer which is obtainable by free-radical copolymerization of at least one N-vinyllactam, at least one anionogenic monomer and optionally further α,β-ethylenically unsaturated compounds copolymerizable therewith, in the presence of a polymer component with repeat units which have ether groups or which are derived from vinyl alcohol.

17 Claims, No Drawings

COSMETIC AGENT CONTAINING AT LEAST ONE COPOLYMER HAVING N-VINYLLACTAM UNITS

The present invention relates to a cosmetic composition which comprises at least one water-soluble or water-dispersible copolymer which is obtainable by two-stage free-radical copolymerization of at least one N-vinyllactam, at least one anionogenic monomer, at least one open-chain monomer different therefrom and optionally further α,β-ethylenically unsaturated compounds copolymerizable therewith in the presence of a polymer component with repeat units which have ether groups or which are derived from vinyl alcohol.

Polymers are used widely in cosmetics and medicine. In soaps, creams and lotions, for example, they are usually used as formulation agents, e.g. as thickeners, foam stabilizer or water absorbent or else to alleviate the irritative effect of other ingredients or to improve the dermal application of active ingredients. By contrast, their aim in hair cosmetics is to influence the properties of the hair, for example to set the hair.

For example, hairstyles are set using vinyllactam homo- and copolymers and carboxylate-containing polymers. Requirements on hair-setting resins are, for example, strong hold at high atmospheric humidity, elasticity, ability to be washed out of the hair, compatibility in the formulation and a pleasant feel of the hair treated therewith.

The provision of products with a complex profile of properties often presents difficulties. Thus, there is a need for polymers for cosmetic compositions which are able to form essentially smooth, nonsticky films which impart a pleasant feel to the hair and to the skin and at the same time have a good setting action or conditioning action. In addition, esthetic requirements are increasingly imposed by the consumer on cosmetic and pharmaceutical products. Thus, in the case of such products, a preference for formulations in the form of gels, in particular clear gels, is currently observed. In the formulation of clear gels for cosmetics, the compatibility of the cosmetic active ingredients with the gel base is particularly important. Known cosmetic gel formulations are based, for example, on polyvinylformamide or on a combination of polyvinylpyrrolidone with suitable thickeners, on vinylpyrrolidone/vinyl acetate copolymers or on copolymers of vinylpyrrolidone with cationogenic or cationic comonomers.

EP-A-0 251 444 describes terpolymers of vinylpyrrolidone, tert-butyl (meth)acrylate and (meth)acrylic acid and the use thereof in hair-treatment compositions.

DE-A-37 16 380 describes compositions for treating the skin or hair in the form of an aerosol foam which comprise, as foaming agent, at least one partially acetylated polyvinyl alcohol and further ingredients, such as cationic, anionic or amphoteric agents.

U.S. Pat. No. 5,632,977 describes haircare compositions which comprise a polymer which contains copolymerized N-vinylformamide and further monomers, e.g. monomers with amine groups and lactams, such as N-vinylpyrrolidone.

JP-A-0525 5057 describes a skin protectant which comprises a mixture of polyvinyl alcohol and polyvinylpyrrolidone.

None of the abovementioned documents describes the polymerization of free-radically polymerizable unsaturated compounds (monomer) in the presence of free-prepared polymers which for their part do not have any carbon-carbon double bonds.

DE-A-44 34 986 describes a process for the preparation of aqueous solutions of poly(N-vinyl-ε-caprolactam) by polymerization in the presence of a polymeric protective colloid. The compounds here may, for example, be polyvinyl alcohol, partially esterified polyvinyl acetate, polyalkyl vinyl ether and mixtures thereof. In very general terms and without any proof by an application example, the suitability of aqueous solutions of poly(N-vinyl-ε-caprolactam) for cosmetic preparations, for example hair lacquer, hair spray and skin-cosmetic preparations, is described.

JP-A-0618 4251 describes graft copolymers of N-vinylacetamide, optionally in combination with further vinyl monomers, onto polyvinyl alcohol. These graft copolymers are suitable for water-soluble packagings.

WO 99/04750 describes a process for the preparation of polymers by free-radical polymerization of ethylenically unsaturated monomers in the presence of polyalkylene oxide-containing silicone derivatives.

DE-A-44 09 903 describes graft polymers containing N-vinyl units, processes for their preparation and their use. In this process, monoethylenically unsaturated monomers are grafted onto a graft base which is a polymer which contains in each case at least 5% by weight of units of the formulae

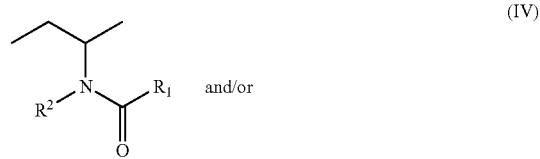

(IV)

(V)

where $R^1$, $R^2$=H or $C_1$-$C_6$-alkyl. Suitable monoethylenically unsaturated monomers are all ethylenically unsaturated monomers whose polymerization is not inhibited by the amine groups in free or in salt form, such as, for example, monoethylenically unsaturated mono- and dicarboxylic acids, their salts and esters with $C_1$-$C_{30}$-alcohols. A suitability of these graft copolymers as active ingredient in cosmetic formulations is not described.

WO 96/34903 describes graft polymers containing N-vinyl units, processes for their preparation and their use. Here, N-vinylcarboxamides and optionally further comonomers are grafted onto a polyalkylene oxide graft base and the resulting polymer is then at least partially saponified. A suitability of these graft copolymers as active ingredient in cosmetic formulations is not described.

DE-A-29 24 663 describes a process for the preparation of aqueous dispersions in which a monomer a) capable of forming water-soluble polymers is polymerized in the presence of a water-soluble polymer b) different therefrom. The monomers a) used are (meth)acrylamides, (meth)acrylic acid, their halogen derivatives and salts, and esters of (meth)acrylic acid with amino alkanols. The polymer b) has at least one hydrophilic structural unit and is chosen, for example, from polyalkylene glycols, polyvinyl alcohol, etc. In addition to a large number of possible uses of these dispersions, a use as additive for medicaments or cosmetics is also described in very general terms and without proof by a working example.

The unpublished German patent application P 100 412 11.4 describes the use of graft copolymers obtainable by free-radical graft copolymerization of at least one open-chain N-vinylamide compound and optionally at least one further monomer, copolymerizable therewith, on a polymeric graft base, for cosmetic applications.

It is an object of the present invention to provide cosmetic compositions with good performance properties. These should impart a pleasant feel to the hair or the skin treated therewith and at the same time have a good conditioning action or setting action. Preferably, they should be suitable for the preparation of products in the form of gels.

We have found that this object is achieved by a cosmetic composition which comprises at least one copolymer obtainable by two-stage free-radical copolymerization of at least one N-vinyllactam, at least one anionogenic monomer and at least one further monomer different therefrom in the presence of a water-soluble polymer component which essentially does not comprise any carbon-carbon double bonds.

The present invention therefore provides a cosmetic or pharmaceutical composition comprising, in a cosmetically acceptable carrier, at least one water-soluble or water-dispersible copolymer A), which is obtainable by two-stage free-radical copolymerization of a monomer mixture of
a) 20 to 99.9% by weight, based on the total weight of components a) to d), of at least one N-vinyllactam,
b) 0.1 to 30% by weight, based on the total weight of components a) to d), of at least one compound with a free-radically polymerizable, α,β-ethylenically unsaturated double bond and at least one anionogenic group per molecule,
c) 0.1 to 65% by weight, based on the total weight of components a) to d), of at least one free-radically polymerizable compound chosen from
   c1) open-chain, α,β-ethylenically unsaturated compounds of the formula I

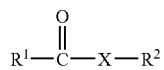

(I)

where
one of the radicals $R^1$ or $R^2$ is a group of the formula $CH_2=CR^3-$ where $R^3=H$ or $C_1$-$C_4$-alkyl and the other is H, alkyl, hydroxyalkyl, aminoalkyl, the N-alkyl and N,N-dialkyl derivatives thereof or a polyether radical with at least 5 alkylene oxide units, and X is O or $NR^4$, where $R^4$ is hydrogen, $C_1$-$C_7$-alkyl or a polyether radical having at least 5 alkylene oxide units,
   c2) compounds with a free-radically polymerizable, α,β-ethylenically unsaturated double bond and at least one anionic or cationic group per molecule,
d) 0 to 15% by weight, based on the total weight of components a) to d), of at least one copolymerizable monomer which is different from a) to c)

in the presence of at least one water-soluble component e) which is chosen from
e1) polyether-containing compounds, and/or
e2) polymers which have at least 50% by weight of repeat units which are derived from vinyl alcohol, where:
i) the monomers a) and optionally at least some of the monomers c) are polymerized in the presence of at least some of component e) to give a first polymer A1), and
ii) the monomers b) and if present d) and the monomers c) and compounds e) not already used in step i) are added and polymerized to give the copolymer A).

For the purposes of the present invention, the expressions $C_1$-$C_7$-alkyl, $C_1$-$C_4$-alkyl, $C_8$-$C_{30}$-alkyl and $C_2$-$C_{22}$-alkyl include straight-chain and branched alkyl groups. Suitable short-chain alkyl groups are, for example, straight-chain or branched $C_1$-$C_7$-alkyl, preferably $C_1$-$C_6$-alkyl and particularly preferably $C_1$-$C_4$-alkyl groups. These include, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, octyl, etc.

Suitable longer-chain $C_8$-$C_{30}$-alkyl or $C_8$-$C_{30}$-alkenyl groups are straight-chain and branched alkyl or alkenyl groups. These are preferably predominantly linear alkyl radicals, as also occur in natural or synthetic fatty acids and fatty alcohols and also oxo alcohols, which may optionally be additionally mono-, di- or polyunsaturated. Preference is given to $C_8$-$C_{22}$-alkyl or -alkenyl groups. These include, for example, n-hexyl(ene), 2- and 3-methylpentyl(ene), n-heptyl(ene), 2- and 3-methylhexyl(ene), n-octyl(ene), 2-, 3- and 4-methylheptyl(ene), 2- and 3-ethylhexyl(ene), n-nonyl(ene), n-decyl(ene), n-undecyl(ene), n-dodecyl(ene), n-tridecyl(ene), n-tetradecyl(ene), n-pentadecyl(ene), n-hexadecyl(ene), n-heptadecyl(ene), n-octadecyl(ene), n-nonadecyl(ene), etc.

Cycloalkyl is preferably $C_5$-$C_8$-cycloalkyl, such as cyclopentyl, cyclohexyl, cycloheptyl or cyclooctyl.

Heterocycloalkyl includes saturated cycloaliphatic radicals having, in general, 4 to 8, preferably 5 to 7, ring atoms in which 1, 2 or 3 of the ring atoms are a heteroatom chosen from oxygen, sulfur and optionally substituted nitrogen. These include, for example, pyrrolidinyl, piperidinyl, imidazolidinyl, pyrazolidinyl, oxazolidinyl, morpholidinyl, thiazolidinyl, isothiazolidinyl, isoxazolidinyl, piperazinyl, tetrahydrothiophenyl, tetrahydrofuranyl, tetrahydropyranyl and dioxanyl.

Aryl is preferably phenyl, tolyl, xylyl or naphthyl.

Arylalkyl is preferably benzyl or phenylethyl.

In the text below, compounds which may be derived from acrylic acid and methacrylic acid may sometimes be referred to in abbreviated form by adding the syllable "(meth)" to the compound derived from acrylic acid.

The compositions according to the invention can be formulated under standard conditions (20° C.) advantageously as gels. "Gel-like consistency" indicates compositions which have a higher viscosity than a liquid and which are self-supporting, i.e. they retain a shape given to them without a shape-stabilizing coating. In contrast to solid formulations, however, gel-like formulations can be readily deformed under the application of shear forces.

The viscosity of the gel-like compositions is preferably in a range from 600 to 60 000 mPas.

For the purposes of the present invention, water-soluble compounds (monomers, polymers) are to be understood as meaning compounds which dissolve to at least 1 g/l at 25° C. in water. Water-dispersible polymers are to be understood as meaning polymers which break down into dispersible particles under the application of shear forces, for example by stirring.

The copolymers A) according to the invention and used for the preparation of the cosmetic compositions according to the invention preferably do not contain any groups containing a silicon atom.

The free-radical copolymerization of the monomer components a), b) and c) and optionally d) in the presence of at least one compound of component e) gives copolymers A) with advantageous properties. This may result, for example, from an at least partial grafting onto component e) as graft base. However, mechanisms other than grafting are also conceivable. Component A) very generally comprises the process products of the free-radical copolymerization, which are to be understood as meaning, for example, pure graft polymers, mixtures of graft polymers with ungrafted compounds of component e), homo- and copolymers of monomers a) to c) and optionally d), and any mixtures.

The preparation of the copolymers A) according to the invention and used according to the invention in cosmetics takes place in two stages, step i) obligatorily using the N-vinyllactams a) and step ii) obligatorily using the monomers b) with anionogenic (usually acidic) functional groups. The sequential copolymers which result in this process are suitable in a particularly advantageous manner for the preparation of gel formulations and have very good compatibility with a large number of active ingredients and auxiliaries used in cosmetics, especially with polymers.

The copolymer A) comprises 20 to 99.9% by weight, preferably 20 to 90% by weight, of at least one copolymerized N-vinyllactam. Suitable N-vinyllactams are those which, in addition to the amide function, have 3 to 6 ring carbon atoms and derivatives thereof which may have, for example, one or more $C_1$-$C_6$-alkyl substituents, such as methyl, ethyl, n-propyl, isopropyl, n-butyl, sec-butyl, tert-butyl, etc. These include, for example, N-vinylpyrrolidone, N-vinylpiperidone, N-vinylcaprolactam, N-vinyl-5-methyl-2-pyrrolidone, N-vinyl-5-ethyl-2-pyrrolidone, N-vinyl-6-methyl-2-piperidone, N-vinyl-6-ethyl-2-piperidone, N-vinyl-7-methyl-2-caprolactam, N-vinyl-7-ethyl-2-caprolactam, etc. Preference is given to using N-vinyllactams which have 3 to 5 ring carbon atoms. Particular preference is given to N-vinylpyrrolidone and N-vinylcaprolactam.

The monomers of component a) are used according to the invention in the 1st step of the copolymerization.

The use of at least one component b) in the preparation of the copolymers A) is advantageous, for example, in order to obtain copolymers A) which are suitable for modifying the rheological properties of homogeneous-phase or heterogeneous-phase compositions. "Modifications of rheological properties" is understood to mean, inter alia, the change in flow properties, the increase in the viscosity of liquids, the improvement in the thixotropic properties of gels, the solidification of gels and waxes, etc. It is of course also possible to use known substances customary as thickeners for establishing the rheological properties of the cosmetic compositions according to the invention.

The anionogenic groups of compound b) are preferably chosen from carboxylic acid, sulfonic acid and phosphonic acid groups.

Suitable compounds b) are e.g. $\alpha,\beta$-ethylenically unsaturated mono-and/or dicarboxylic acids and their half-esters and anhydrides, such as acrylic acid, methacrylic acid, fumaric acid, maleic acid, itaconic acid, crotonic acid, maleic anhydride, monobutyl maleate, etc. Suitable compounds b) are also acrylamidoalkanesulfonic acids, such as 2-acrylamido-2-methylpropanesulfonic acid. Preference is given to using acrylic acid and/or methacrylic acid.

The monomers of component b) are used according to the invention in the 2nd step of the copolymerization. Any neutralization of the anionogenic group takes place only after the polymerization or during the course of formulation.

Component c) is chosen from
c1) open-chain, $\alpha,\beta$-ethylenically unsaturated compounds of the formula I

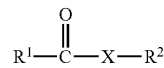

(I)

where
one of the radicals $R^1$ or $R^2$ is a group of the formula $CH_2=CR^3$— where $R^3$=H or $C_1$-$C_4$-alkyl and the other is H, alkyl, hydroxyalkyl, aminoalkyl, the N-alkyl and N,N-dialkyl derivatives thereof or a polyether radical with at least 5 alkylene oxide units, and
X is O or $NR^4$, where $R^4$ is hydrogen, $C_1$-$C_7$-alkyl or a polyether radical having at least 5 alkylene oxide units,
c2) compounds with a free-radically polymerizable, $\alpha,\beta$-ethylenically unsaturated double bond and at least one anionic or cationic group per molecule, and mixtures thereof.

The compounds c1) are preferably chosen from N-vinylamides of saturated monocarboxylic acids, amides of $\alpha,\beta$-ethylenically unsaturated monocarboxylic acids and their N-alkyl, N-polyalkylene glycol, N,N-dialkyl, aminoalkyl, (N-alkylamino)alkyl, (N,N-dialkylamino)alkyl and N,N-di(polyalkylene glycol) derivatives, esters of vinyl alcohol with monocarboxylic acids, alkyl(meth)acrylates, hydroxyalkyl (meth)acrylates, polyether acrylates and mixtures thereof. Suitable polyalkylene glycol radicals are derived, for example, from polyethylene glycols, polypropylene glycols, polytetrahydrofurans and alkylene oxide copolymers. Suitable alkylene oxides for the preparation of alkylene oxide copolymers are, for example, ethylene oxide, propylene oxide, epichlorohydrin, 1,2- and 2,3-butylene oxide. The alkylene oxide copolymers may contain the copolymerized alkylene oxide units in random distribution or in the form of blocks. Preference is given to ethylene oxide/propylene oxide copolymers.

Preferred monomers c1) are primary amides of $\alpha,\beta$-ethylenically unsaturated monocarboxylic acids, such as acrylamide, methacrylamide, ethacrylamide, etc. Particular preference is given to using acrylamide.

Preferred monomers c1) are also amides of $\alpha,\beta$-ethylenically unsaturated mono- and dicarboxylic acids with mono- and dialkylamines which have 1 to 30 carbon atoms, preferably 1 to 22 carbon atoms, per alkyl radical. These include, preferably, amides with short-chain mono- and di-$C_1$-$C_7$-alkylamines, such as N-methyl(meth)acrylamide, N-ethyl (meth)acrylamide, N-(n-propyl)(meth)acrylamide, N-isopropyl(meth)acrylamide, N-(tert-butyl)(meth)acrylamide, N,N-dimethyl(meth)acrylamide, etc. Suitable monomers c1) are also amides which have, on the amide nitrogen, one or two substituents chosen from $C_8$-$C_{30}$-alkyl, $C_8$-$C_{30}$-alkenyl, cycloalkyl-$C_2$-$C_{22}$-alkyl, cycloalkyl-$C_2$-$C_{22}$-alkenyl, aryl-$C_2$-$C_{22}$-alkyl or aryl-$C_2$-$C_{22}$-alkenyl.

These include, for example, n-octyl(meth)acrylamide, 1,1, 3,3-tetramethylbutyl(meth)acrylamide, ethylhexyl(meth) acrylamide, n-nonyl(meth)acrylamide, n-decyl(meth)acrylamide, n-undecyl(meth)acrylamide, tridecyl(meth) acrylamide, myristyl(meth)acrylamide, pentadecyl(meth) acrylamide, palmityl(meth)acrylamide, heptadecyl(meth) acrylamide, nonadecyl(meth)acrylamide, arachinyl(meth) acrylamide, behenyl(meth)acrylamide, lignocerenyl(meth) acrylamide, cerotinyl(meth)acrylamide, melissinyl(meth) acrylamide, palmitoleinyl(meth)acrylamide, oleyl(meth)

acrylamide, linolyl(meth)acrylamide, linolenyl(meth)acrylamide, stearyl(meth)acrylamide, lauryl(meth)acrylamide and mixtures thereof. Suitable monomers c1) are also the N-alkylamides, N,N'-dialkylamides, N-alkyldiamides and N,N'-dialkyldiamides of maleic acid.

Further suitable compounds c1) are the esters of the abovementioned α,β-ethylenically unsaturated mono- and dicarboxylic acids with aminoalcohols, preferably $C_2$-$C_{12}$-aminoalcohols, which are $C_1$-$C_8$-dialkylated on the amine nitrogen. These include, for example, N,N-dimethylaminomethyl(meth)acrylate, N,N-dimethylaminoethyl(meth)acrylate, N,N-diethylaminoethyl(meth)acrylate, N,N-dimethylaminopropyl(meth)acrylate, N,N-diethylaminopropyl(meth)acrylate, N,N-dimethylaminocyclohexyl(meth)acrylate, etc. Preference is given to using N,N-dimethylaminopropylacrylate and N,N-dimethylaminopropyl(meth)acrylate.

Suitable monomers c1) are also the amides of the abovementioned α,β-ethylenically unsaturated mono- and dicarboxylic acids with diamines which have a tertiary and a primary or secondary amino group. These include, for example, N-[2-(dimethylamino)ethyl]acrylamide, N-[2-(dimethylamino)ethyl]methacrylamide, N-[3-(dimethylamino)propyl]acrylamide, N-[3-(dimethylamino)propyl]methacrylamide, N-[4-(dimethylamino)butyl]acrylamide, N-[4-(dimethylamino)butyl]methacrylamide, N-[2-(diethylamino)ethyl]acrylamide, N-[4-(dimethylamino)cyclohexyl]acrylamide, N-[4-(dimethylamino)cyclohexyl]methacrylamide, etc. Particular preference is given to using N-[3-(dimethylamino)propyl]methacrylamide (DMAPMA). N-vinylamides suitable as monomers c1) are, for example, N-vinylformamide, N-vinyl-N-methylformamide, N-vinylacetamide, N-vinyl-N-methylacetamide, N-vinyl-N-ethylacetamide, N-vinylpropionamide, N-vinyl-N-methylpropionamide, N-vinylbutyramide and mixtures thereof. Preference is given to using N-vinylformamide.

Esters of vinyl alcohol with monocarboxylic acids which are suitable as monomers c1) are, for example, vinyl formate, vinyl acetate, vinyl propionate, vinyl n-butyrate, vinyl stearate and vinyl laurate. Preference is given to using vinyl acetate.

Preferred compounds of component c1) are also the adequately water-soluble esters of α,β-ethylenically unsaturated mono- or dicarboxylic acids with $C_1$-$C_3$-alkanols. These include, for example, methyl (meth)acrylate, methyl ethacrylate, ethyl (meth)acrylate, n-propyl acrylate and mixtures thereof. Preference is given to using ethyl acrylate. Also suitable as monomers c1) are, however, esters of α,β-ethylenically unsaturated mono- or dicarboxylic acids with $C_4$-$C_{30}$-alkanols, preferably $C_4$-$C_{22}$-alkanols.

These include, preferably the esters of acrylic acid, methacrylic acid or ethacrylic acid with a saturated or mono- or polyunsaturated $C_8$-$C_{18}$-alcohol, such as octyl (meth)acrylate, 2-ethylhexyl (meth)acrylate, nonyl (meth)acrylate, decycl (meth)acrylate, lauryl (meth)acrylate, pentadecyl (meth)acrylate, palmityl (meth)acrylate, arrachinyl (meth)acrylate, myristyl (meth)acrylate, cetyl (meth)acrylate, stearyl (meth)acrylate, lignocerenyl (meth)acrylate, cerotinyl (meth)acrylate, melissinyl (meth)acrylate, palmitoleinyl (meth)acrylate, oleyl (meth)acrylate, behenyl (meth)acrylate, cyclohexylethyl (meth)acrylate, cyclohexyl-tert-butyl (meth)acrylate, etc.

Suitable monomers c1) are also polyether acrylates, which for the purposes of the invention are generally to be understood as esters of α,β-ethylenically unsaturated mono- and dicarboxylic acids with polyetherols. Suitable polyetherols are linear or branched substances which have terminal hydroxyl groups and which contain ether bonds. In general, they have a molecular weight in the range from about 150 to 20 000. Suitable polyetherols are the abovementioned polyalkylene glycols. Preference is given to polyether acrylates of the formula II

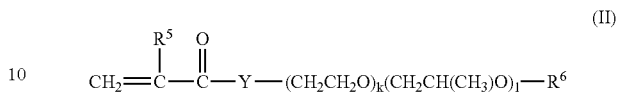

in which
the order of the alkylene oxide units is arbitrary,
k and l independently of one another, are an integer from 0 to 500, where the sum of k and l is at least 5,
$R^5$ is hydrogen or $C_1$-$C_8$-alkyl, and
$R^6$ is hydrogen or $C_1$-$C_6$-alkyl,
Y is O or $NR^7$, where $R^7$ is hydrogen, $C_1$-$C_8$-alkyl or $C_5$-$C_8$-cycloalkyl.
k is preferably an integer from 1 to 500, in particular 3 to 250.
l is preferably an integer from 0 to 100.

Preferably, $R^5$ is hydrogen, methyl, ethyl, n-propyl, isopropyl, n-butyl, sec-butyl, tert-butyl, n-pentyl or n-hexyl, in particular hydrogen, methyl or ethyl.

$R^6$ in the formula II is preferably hydrogen, methyl, ethyl, n-propyl, isopropyl, n-butyl, sec-butyl, n-pentyl or n-hexyl.

Y in the formula II is preferably O or NH.

Suitable polyether acrylates c1) are, for example, the polycondensation products of the abovementioned α,β-ethylenically unsaturated mono- and/or dicarboxylic acids and their acid chlorides, acid amides and anhydrides with polyetherols. Suitable polyetherols can be prepared readily by reacting ethylene oxide, 1,2-propylene oxide and/or epichlorohydrin with a starting molecule such as water or a short-chain alcohol $R^6$—OH. The alkylene oxides can be used individually, alternately one after the other or as a mixture. The polyether acrylates c1) can be used alone or in mixtures for the preparation of the polymers used according to the invention.

Hydroxyalkyl (meth)acrylates suitable as monomers c1) are preferably hydroxy-$C_1$-$C_4$-alkyl (meth)acrylates, such as, for example, hydroxyethyl (meth)acrylate, hydroxy-n-propyl (meth)acrylate, etc.

The anionic compounds c2) are preferably chosen from the salts of the above-described anionogenic compounds b) obtainable by neutralization with a base. Suitable bases for the neutralization are alkali metal bases, such as sodium hydroxide solution, potassium hydroxide solution, sodium carbonate, sodium hydrogencarbonbate, potassium carbonate or potassium hydrogencarbonate and alkaline earth metal bases, such as calcium hydroxide, calcium oxide, magnesium hydroxide or magnesium carbonate, and ammonia and amines. In order that a compound is assigned to component c2), it must already be present in salt form during the polymerization. For this purpose, a neutralization of corresponding compounds b) must take place prior to polymerization.

Cationic compounds c2) are obtainable by partial or complete protonation or quaternization of the amine groups of the abovementioned amine-containing monomers. Suitable acids for the protonation are, for example, carboxylic acids, such as lactic acid or mineral acids, such as phosphoric acid, sulfuric acid or hydrochloric acid. Suitable alkylating agents for the quaternization are, for example, $C_1$-$C_4$-alkyl halides and sulfates. These include, for example, ethyl chloride, ethyl bromide, methyl chloride, methyl bromide, dimethyl sulfate and diethyl sulfate.

The abovementioned monomers c) can be used individually or in the form of mixtures. The monomers c) can in principle in each case be used partially or completely in the first and the second stage of the copolymerization. N-vinylamides c) are usually used in the first stage.

Suitable monomers d) are, for example, vinylaromatics, such as styrene, α-methylstyrene, o-chlorostyrene and vinyltoluene, vinyl halides, such as vinyl chloride, vinylidene halides, such as vinylidene chloride, monoolefins, such as ethylene and propylene, nonaromatic hydrocarbons with at least two conjugated double bonds, such as butadiene, isoprene and chloroprene and mixtures thereof.

The compounds of component e) used according to the invention essentially do not contain any carbon-carbon double bonds. According to a suitable embodiment, the compounds of component e) do not contain any silicon-containing groups.

Suitable polyether-containing compounds e1) are generally water-soluble or water-dispersible, nonionic polymers which have polyalkylene glycol groups. The proportion of polyalkylene glycol groups is preferably at least 40% by weight, based on the total weight of the compound e1). Polyether-containing compounds e1) which can be used are, for example, the abovementioned polyalkylene glycols, polyesters based on polyalkylene glycols, and polyether urethanes.

Depending on the nature of the monomer building blocks used for their preparation, the polyether-containing compounds e1) contain the following structural units:
—(CH$_2$)$_2$—, —(CH$_2$)$_3$—, —(CH$_2$)$_4$—, —CH$_2$—CH(R$^8$)—O—, in which R$^8$ is C$_1$-C$_{24}$-alkyl, preferably C$_1$-C$_4$-alkyl.

The compounds e1) can additionally have bridging groups, which are chosen, for example, from:
—C(=O)—O—, —O—C(=O)—O—, —C(=O)—NR$^a$—, —O—C(=O)—NR$^a$—, —NR$^b$—(C=O)—NR$^a$— in which R$^a$ and R$^b$, independently of one another, are hydrogen, C$_1$-C$_{30}$-alkyl, preferably C$_1$-C$_4$-alkyl or cycloalkyl.

As polyether e1), preference is given to using polymers of the formula III with a molecular weight of >300

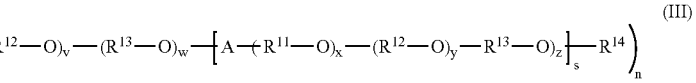

in which the variables, independently of one another, have the following meanings:
R$^{10}$ is hydrogen, C$_1$-C$_{24}$-alkyl, R$^8$—C(=O)—, R$^8$—NH—C(=O)—, polyalcohol radical;
R$^{14}$ is hydrogen, C$_1$-C$_{24}$-alkyl, R$^8$—C(=O)—, R$^8$—NH—C(=O)—;
R$^{11}$ to R$^{13}$ are —(CH$_2$)$_2$—, —(CH$_2$)$_3$—, —(CH$_2$)$_4$—, —CH$_2$—CH(R$^8$)—, —CH$_2$—CHOR$^9$—CH$_2$—;
R$^8$ is C$_1$-C$_{24}$-alkyl;
R$^9$ is hydrogen, C$_1$-C$_{24}$-alkyl, R$^8$—C(=O)—, R$^8$—NH—C(=O)—;
A is —C(=O)—O—, —C(=O)—B—C(=O)—O—, —C(=O)—NH—B—NH—C(=O)—O;
B is —(CH$_2$)$_t$—, optionally substituted cycloalkylene, heterocycloalkylene or arylene;
n is 1 to 1 000, preferably 1 to 200;
s is 0 to 1 000, preferably 0 to 100;
t is 2 to 12, preferably 1 to 500;
u is 1 to 5 000, preferably 1 to 500;
v is 0 to 5 000, preferably 1 to 500;
w is 0 to 5 000, preferably 1 to 500;
x is 0 to 5 000, preferably 1 to 500;
y is 0 to 5 000, preferably 1 to 500;
z is 0 to 5 000, preferably 1 to 500.

The terminal primary hydroxyl groups of the polyethers prepared on the basis of polyalkylene oxides, and the secondary OH groups of polyglycerol may here be present either freely in unprotected form, or else be etherified or esterified with alcohols of chain length C$_1$-C$_{24}$ or with carboxylic acids of chain length C$_1$-C$_{24}$, or be reacted with isocyanates to give urethanes. Preference is given to using polyether urethanes.

Preferred representatives of the abovementioned alkyl radicals which may be mentioned are branched or unbranched C$_1$-C$_{12}$, particularly preferably C$_1$-C$_6$-alkyl chains.

The molecular weight of the polyethers is in the range greater than 300 (number-average), preferably in the range from 300 to 100 000, particularly preferably in the range from 500 to 50 000, very particularly preferably in the range from 800 to 40 000.

Advantageously, homopolymers of ethylene oxide or copolymers with an ethylene oxide content of 40 to 99% by weight are used. For the preferred ethylene oxide polymers, the proportion of copolymerized ethylene oxide is thus 40 to 100 mol %. Suitable comonomers for these copolymers are propylene oxide, butylene oxide and/or isobutylene oxide. Copolymers of ethylene oxide and propylene oxide, copolymers of ethylene oxide and butylene oxide, and copolymers of ethylene oxide, propylene oxide and at least one butylene oxide, are suitable. The ethylene oxide content of the copolymers is preferably 40 to 99 mol %, the propylene oxide content is 1 to 60 mol % and the content of butylene oxide in the copolymers is 1 to 30 mol %. In addition to straight-chain homo- or copolymers, it is also possible to use branched homo- or copolymers as polyether-containing compounds e1).

Branched polymers can be prepared by adding ethylene oxide and optionally also propylene oxide and/or butylene oxide onto polyalcohol radicals, e.g. onto pentaerythritol, glycerol or onto sugar alcohols such as D-sorbitol and D-mannitol, and also onto polysaccharides, such as cellulose and starch. The alkylene oxide units may be in random distribution or in the form of blocks within the polymer.

It is, however, also possible to use polyesters of polyalkylene oxides and aliphatic or aromatic dicarboxylic acids, e.g. oxalic acid, succinic acid, adipic acid and terephthalic acid with molar masses of 1 500 to 25 000, as described, for example, in EP-A-0 743 962, as polyether-containing compound. Furthermore, it is also possible to use polycarbonates by reacting polyalkylene oxides with phosgene or carbonates, such as, for example, diphenyl carbonate, and also polyurethanes by reacting polyalkylene oxides with aliphatic and aromatic diisocyanates.

In a preferred embodiment, a component e1) which comprises at least one polyether urethane is used for the preparation of the copolymers A).

Suitable polyether urethanes are the condensation products of polyetherpolyols, such as polyetherdiols, with polyisocyanates, such as diisocyanates. Suitable polyetherpolyols are the abovementioned polyalkylene glycols which are obtainable, for example, from the polymerization of cyclic ethers, such as tetrahydrofuran, or from the reaction of one or more alkylene oxides with a starting molecule which has two or more active hydrogen atoms.

Suitable polyisocyanates are chosen from compounds with 2 to 5 isocyanate groups, isocyanate prepolymers with an average number of from 2 to 5 isocyanate groups, and mixtures thereof. These include, for example, aliphatic, cycloaliphatic and aromatic di-, tri- and polyisocyanates. Suitable diisocyanates are, for example, tetramethylene diisocyanate, hexamethylene diisocyanate, 2,3,3-trimethylhexamethylene diisocyanate, 1,4-cyclohexylene diisocyanate, isophorone diisocyanate, 1,4-phenylene diisocyanate, 2,4- and 2,6-toluylene diisocyanate and isomer mixtures thereof (e.g. 80% 2,4- and 20% 2,6-isomer), 1,5-naphthylene diisocyanate, 2,4- and 4,4'-diphenylmethane diisocyanate. A suitable triisocyanate is, for example, triphenylmethane 4,4', 4"-triisocyanate. Also suitable are isocyanate prepolymers and polyisocyanates which are obtainable by addition of the abovementioned isocyanates onto polyfunctional hydroxyl- or amine-containing compounds. Also suitable are polyisocyanates which arise as a result of biuret or isocyanurate formation. Preference is given to using hexamethylene diisocyanate, trimerized hexamethylene diisocyanate, isophorone diisocyanate, 2,4-toluylene diisocyanate, 2,6-toluylene diisocyanate, and mixtures thereof.

Also suitable as graft base are polymers e2) which have at least 50% by weight of vinyl alcohol units. These polymers preferably contain at least 70% by weight, very particularly preferably at least 80% by weight, of polyvinyl alcohol units. Such polymers are usually prepared by polymerization of a vinyl ester and subsequent at least partial alcoholysis, aminolysis or hydrolysis. Preference is given to vinyl esters of linear and branched $C_1$-$C_{12}$-carboxylic acids, and vinyl acetate is very particularly preferred. The vinyl esters can of course also be used in a mixture.

Suitable vinyl ester comonomers for the synthesis of the graft base e2) are, for example, N-vinylcaprolactam, N-vinylpyrrolidone, N-vinylimidazole, N-vinyl-2-methylimidazole, N-vinyl-4-methylimidazole, 3-methyl-1-vinylimidazolium chloride, 3-methyl-1-vinylimidazolium methylsulfate, diallylammonium chloride, styrene, alkylstyrenes.

The graft base e2) is prepared by known processes, for example solution, precipitation, suspension or emulsion polymerization using compounds which form free radicals under the polymerization conditions. The polymerization temperatures are usually in the range from 30 to 200° C., preferably 40 to 110° C. Suitable initiators are, for example, azo and peroxy compounds, and the customary redox initiator systems, such as combinations of hydrogen peroxide and reducing compounds, for example sodium sulfite, sodium bisulfite, sodium formaldehyde sulfoxilate and hydrazine. These systems can optionally still also contain small amounts of a heavy metal salt.

To prepare the graft base e2), the ester groups of the original monomers and optionally further monomers are at least partially cleaved after the polymerization by hydrolysis, alcoholysis or aminolysis. In the text below, this process step is generally referred to as saponification. The saponification takes place in a manner known per se by adding a base or acid, preferably by adding a sodium or potassium hydroxide solution in water and/or alcohol. Particular preference is given to using methanolic sodium or potassium hydroxide solutions. The saponification is carried out at temperatures in the range from 10 to 80° C., preferably in the range from 20 to 60° C. The degree of saponification depends on the amount of base or acid used, on the saponification temperature, the saponification time and the water content in the solution.

Particularly preferred graft bases e2) are polymers which are prepared by homopolymerization of vinyl acetate and subsequent at least partial hydrolysis, alcoholysis or aminolysis. Such polymers containing polyvinyl alcohol units are available under the name Mowiol®.

The copolymer A) according to the invention and used in the compositions according to the invention is preferably obtainable by free-radical copolymerization of
   20 to 90% by weight of at least one N-vinyllactam a),
   1 to 20% by weight of at least one compound b) and
   5 to 65% by weight of at least one compound c)

in the presence of at least one component e).

Particular preference is given to the copolymer A) obtainable by free-radical copolymerization of
a) 20 to 90% by weight of N-vinylpyrrolidone and/or N-vinylcaprolactam,
b) 1 to 20% by weight of (meth)acrylic acid,
c) 5 to 65% by weight of at least one compound chosen from N-vinylamides of saturated monocarboxylic acids, amides of α,β-ethylenically unsaturated monocarboxylic acids, N,N-dialkylaminoalkyl (meth)acrylates, $C_1$-$C_3$-alkyl (meth)acrylates, polyalkylene glycol (meth)acrylates and mixtures thereof, in the presence of at least one component e).

A preferred copolymer A) is, for example, obtainable by free-radical copolymerization of
a) 25 to 80% by weight of N-vinylpyrrolidone and/or N-vinylcaprolactam,
b) 1 to 10% by weight of (meth)acrylic acid,
c1) 5 to 45% by weight of acrylamide,
c2) 0 to 6% by weight of at least one monomer with at least one cationic group per molecule, preferably protonized or quaternized dimethylaminoethyl methacrylate, in the presence of at least one component e).

The quantitative weight ratio of the total amount of components a) to d) relative to component e) is preferably 100:1 to 1:1, particularly preferably 50:1 to 3:1.

The copolymers A) are prepared in accordance with customary processes known to the person skilled in the art, such as, for example solution, precipitation, emulsion, inverse emulsion, suspension or inverse suspension polymerization. Preference is given to solution polymerization.

Step i)

According to the invention, in the first step of the free-radical copolymerization, at least one N-vinyllactam a), optionally at least one monomer c) is polymerized in the presence of at least some of component e) to give the first polymer A1).

Some or all of the monomers used can be initially introduced into the reaction zone. Preferably, the monomers are not introduced into the reaction zone initially, or only some of them are introduced, and the remainder is continuously introduced at the rate of its consumption. The introduction of two or more monomers can take place separately or in mixtures.

The polymerization in step i) takes place in the presence of at least some of component e). This can either be introduced into the reaction zone initially in its entirety at the start of the polymerization or be introduced into the reaction zone partially or completely over the course of the polymerization.

The polymerization in step i) preferably takes place in water as solvent.

The polymerization temperature in step i) is preferably in a range from 30 to 140° C., in particular 50 to 90° C. The polymerization in step i) preferably takes place at a pH of at least 6.0, particularly preferably at least 6.5, in particular at least 7.

The polymer A1) obtained in step i) can be isolated prior to further reaction in step ii) if desired and/or purified by customary methods known to the person skilled in the art. These include, for example, spray drying. The resulting polymers A1) represent novel intermediates which, as well as being used in step ii) of the process according to the invention, can also be used as a basis for the preparation of further polymers (e.g. in the sense of a grafting). The reaction mixture obtained in step i) is preferably used without work-up in the subsequent step ii).

Step ii)

According to the invention, in the second step of the free-radical copolymerization, the prepolymer A1) is reacted with at least one monomer b) to give the copolymer A). If desired, monomers c) can also be used as comonomers in step ii). The monomers d), if used, are obligatorily used as comonomers in step ii). If, in step ii), a remaining part of component e) is used, then this can be introduced into the reaction zone in its entirety at the start of the second polymerization step or during the course of the polymerization.

The monomers used in step ii) are preferably introduced into the reaction zone at the rate of their consumption. Water-soluble monomers can preferably be used as aqueous solution, sparingly water-soluble or water-insoluble, for example as aqueous/alcoholic or alcoholic, solution.

The polymerization in step ii) preferably takes place in a water/$C_1$-$C_4$-alkanol mixture as solvent. For this, preferably up to 50% by weight of at least one alcohol, based on the total amount of solvent, are added to the reaction mixture from step i). Preference is given to water/ethanol mixtures.

The polymerization temperature in step ii) is preferably in a range from 40 to 140° C. The reaction temperature is preferably increased when the monomer addition is complete to at least 90° C., preferably at least 100° C., to complete the polymerization.

The polymerization in step ii) preferably takes place at a pH of less than 6.5, especially at most 6.

The polymerization in both steps usually takes place under atmospheric pressure, although it can also proceed under reduced or increased pressure. A suitable pressure range is between 1 and 5 bar.

To prepare the polymers, the monomers of components a) to d) used can be polymerized in the presence of component e) both using initiators which form free radicals and also by the action of high-energy radiation, which is also to be understood as including the action of high-energy electrons.

Initiators for the free-radical polymerization which can be used in both steps are the peroxo and/or azo compounds customary for this purpose, for example alkali metal or ammonium peroxidisulfates, diacetyl peroxide, dibenzoyl peroxide, succinyl peroxide, di-tert-butyl peroxide, tert-butyl perbenzoate, tert-butyl perpivalate, tert-butyl peroxy-2-ethylhexanoate, tert-butyl permaleate, cumene hydroperoxide, diisopropyl peroxidicarbamate, bis-(o-toloyl) peroxide, didecanoyl peroxide, dioctanoyl peroxide, dilauroyl peroxide, tert-butyl perisobutyrate, tert-butyl peracetate, di-tert-amyl peroxide, tert-butyl hydroperoxide, azobisisobutyronitrile, azobis(2-amidinopropane) dihydrochloride or 2,2'-azobis(2-methylbutyronitrile). Also suitable are initiator mixtures or redox initiator systems, such as, for example, ascorbic acid/iron(II) sulfate/sodium peroxodisulfate, tert-butyl hydroperoxide/sodium disulfite, tert-butyl hydroperoxide/sodium hydroxymethanesulfinate.

Preference is given to using water-soluble initiators.

The amounts of initiator or initiator mixtures used, based on the monomers used, are, for both steps together, generally between 0.01 and 10% by weight, preferably between 0.1 and 5% by weight.

The invention also provides a process for the preparation of at least one water-soluble or water-dispersible copolymer A) by free-radical copolymerization, as described above.

Copolymers A) which contain acid groups can be partially neutralized, with the proviso that the resulting copolymer still contains anionogenic groups corresponding to a copolymerized content of 0.1 to 30% by weight of component b). Suitable bases for the neutralization are those mentioned above for the neutralization of the ionogenic monomers b). Polymers with amine groups can also be converted into cationic groups by reaction ith acids or quaternizing agents, e.g. with alkylating agents, such as $C_1$-$C_4$-alkyl halides or sulfates. Suitable acids and alkylating agents have been mentioned above. As a rule, the resulting salts of the polymers have better solubility in water or dispersibility in water than the non-neutralized or -quaternized polymers.

If, in the preparation of the polymers an organic solvent is used, then this can be removed by customary processes known to the person skilled in the art, e.g. by distillation at reduced pressure. For preservation, customary preservatives may be added to the copolymers. A preferred preservative is ethanol.

The polymer solutions and dispersions can be converted into powder form by various drying processes, such as, for example, spray drying, fluidized spray drying, roll drying or freeze drying. Preference is given to using spray drying. The resulting polymer dry powders can advantageously be converted again into an aqueous solution or dispersion by solution or redispersion in water. Pulverulent copolymers have the advantage of better storability, simpler transportation possibility and usually exhibit a lower tendency toward microbial attack.

The invention also provides the copolymers A).

The cosmetically acceptable carrier is preferably chosen from i) water,
ii) wasser-miscible organic solvents, preferably $C_1$-$C_4$-alkanols,
iii) propellant gases, preferably propane/butane mixtures and dimethyl ether,
iv) oils, fats, waxes,
v) esters of $C_6$-$C_{30}$-monocarboxylic acids with mono-, di- or trihydric alcohols which are different from iv),
vi) saturated acyclic and cyclic hydrocarbons,
vii) fatty acids,
viii) fatty alcohols and mixtures thereof.

The compositions according to the invention preferably have at least one hydrophilic cosmetically or pharmaceutically acceptable carrier. Suitable hydrophilic carriers are chosen from water, 1-, 2- or polyhydric alcohols having, preferably, 1 to 8 carbon atoms, such as ethanol, n-propanol, isopropanol, propylene glycol, glycerol, sorbitol, etc.

To prepare aerosol formulations (sprays), the compositions according to the invention can have at least one propellant gas (propellant). These include, for example, propane, n-butane, n-pentane, $C_3$-$C_5$-alkane mixtures, dimethyl ether, etc.

The compositions according to the invention can have, as carriers, also, for example, an oil or fatty component which is chosen from:

hydrocarbons of low polarity, such as mineral oils; linear saturated hydrocarbons, preferably having more than 8 carbon atoms, such as tetradecane, hexadecane, octadecane, etc.; cyclic hydrocarbons, such as decahydronaphthaline; branched hydrocarbons; animal and vegetable oils; waxes; wax esters; vaseline; esters, preferably esters of fatty acids, such as, for example, esters of $C_1$-$C_{24}$-monoalcohols with $C_1$-$C_{22}$-monocarboxylic acids, such as isopropyl isostearate, n-propyl myristate, isopropyl myristate, n-propyl palmitate, isopropyl palmitate, hexacosanyl palmitate, octacosanyl palmitate, triacontanyl palmitate, dotriacontanyl palmitate, tetratriacontanyl palmitate, hexacosanyl stearate, octacosanyl stearate, triacontanyl stearate, dotriacontanyl stearate, tetratriacontanyl stearate; salicylates, such as $C_1$-$C_{10}$-salicylates, for example, octyl salicylate; benzoate esters, such as $C_{10}$-$C_{15}$-alkyl benzoates, benzyl benzoate; other cosmetic esters, such as fatty acid triglycerides, propylene glycol monolaurate, polyethylene glycol monolaurate, $C_{10}$-$C_{15}$-alkyl lactates, etc. and mixtures thereof.

Suitable silicone oils are e.g. linear polydimethylsiloxanes, poly(methylphenylsiloxanes), cyclic siloxanes and mixtures thereof. The number-average molecular weight of the polydimethylsiloxanes and poly(methylphenylsiloxanes) is preferably in a range from about 1 000 to 150 000 g/mol. Preferred cyclic siloxanes have 4- to 8-membered rings. Suitable cyclic siloxanes are commercially available, e.g. under the name cyclomethicone.

Preferred oil and/or fatty components are chosen from paraffin and paraffin oils; vaseline; natural fats and oils, such as castor oil, soybean oil, peanut oil, olive oil, sunflower oil, sesame oil, avocado oil, cocoa butter, almond oil, peach kernal oil, castor oil, cod-liver oil, lard, spermaceti, spermaceti oil, sperm oil, wheatgerm oil, macadamia nut oil, evening primrose oil, jojoba oil; fatty alcohols, such as lauryl alcohol, myristyl alcohol, cetyl alcohol, stearyl alcohol, oleyl alcohol, cetyl alcohol; fatty acids, such as myristic acid, stearic acid, palmitic acid, oleic acid, linoleic acid, linolenic acid and saturated, unsaturated and substituted fatty acids different therefrom; waxes, such as beeswax, carnauba wax, candililla wax, spermaceti and mixtures of the abovementioned oil and fatty components.

Suitable cosmetically and pharmaceutically compatible oil and fatty components are described in Karl-Heinz Schrader, Grundlagen und Rezepturen der Kosmetika [Cosmetic bases and formulations], 2nd edition, Verlag Hüthig, Heidelberg, pp. 319-355, to which reference is made here.

The cosmetic compositions according to the invention may be skin cosmetic, dermatological or hair cosmetic compositions.

The compositions according to the invention are preferably in the form of a gel, foam, spray, an ointment, cream, emulsion, suspension, lotion, milk or paste. If desired, liposomes or microspheres may also be used. Preferred formulations are gels, foams and sprays. The copolymers A) according to the invention and used in accordance with the invention advantageously have high compatibility with other cosmetic and pharmaceutical ingredients, in particular hair polymers. They are particularly suitable for the preparation of clear, solid gels.

The cosmetically or pharmaceutically active compositions according to the invention can additionally comprise cosmetically and/or dermatologically active ingredients and auxiliaries.

Suitable cosmetically and/or dermatologically active ingredients are, for example, coloring active ingredients, skin and hair pigmentation agents, tinting agents, tanning agents, bleaches, keratin-hardening substances, antimicrobial active ingredients, light filter active ingredients, repellant active incredients, substances with hyperemic activity, substances with keratolytic and keratoplastic activity, antidandruff active ingredients, antiphlogistics, substances which have a keratinizing action, substances which act as antioxidants or as free-radical scavengers, skin moisturizers or humectants, refatting active ingredients, antierythematous or antiallergic active ingredients and mixtures thereof.

Artificially skin-tanning active ingredients which are suitable for tanning the skin without natural or artificial irradiation with UV rays are e.g. dihydroxyacetone, alloxan and walnut shell extract. Suitable keratin-hardening substances are usually active ingredients as are also used in antiperspirants, such as, for example, potassium aluminum sulfate, aluminum hydroxychloride, aluminum lactate, etc. Antimicrobial active ingredients are used in order to destroy microorganisms or to inhibit their growth and thus to serve both as preservatives and also as a deodorizing substance which prevents the formation or the intensity of body odor. These include, for example, customary preservatives known to the person skilled in the art, such as p-hydroxybenzoic esters, imidazolidinylurea, formaldehyde, sorbic acid, benzoic acid, salicylic acid, etc. Such deodorizing substances are, for example, zinc ricinoleate, triclosan, undecylenic acid alkylolamides, triethyl citrate, chlorhexidine, etc. Suitable light filter active ingredients are substances which absorb UV rays in the UV-B and/or UV-A region. Suitable UV filters are, for example, 2,4,6-triaryl-1,3,5-triazines in which the aryl groups may each carry at least one substituent which is preferably chosen from hydroxyl, alkoxy, specifically methoxy, alkoxycarbonyl, specifically methoxycarbonyl and ethoxycarbonyl and mixtures thereof. Also suitable are p-aminobenzoates, cinnamic esters, benzophenones, camphor derivatives and pigments which stop UV rays, such as titanium dioxide, talc and zinc oxide. Suitable repellant active ingredients are compounds which are able to drive away or expel certain animals, in particular insects, from humans. These include, for example, 2-ethyl-1,3-hexanediol, N,N-diethyl-m-toluamide, etc. Suitable substances with hyperemic activity, which stimulate blood flow through the skin, are, for example, essential oils, such as dwarf pine, lavender, rosemary, juniperberry, horse chestnut extract, birch leaf extract, hay seed extract, ethyl acetate, camphor, menthol, peppermint oil, rosemary extrakt, eucalyptus oil, etc. Suitable keratolytic and keratoplastic substances are, for example, salicylic acid, potassium thioglycolate, thioglycolic acid and salts thereof, sulfur, etc. Suitable antidandruff ingredients are, for example, sulfur, sulfur polyethylene glycol sorbitan monooleate, sulfur ricinol polyethoxylate, zinc pyrithione, aluminum pyrithione, etc. Suitable antiphlogistics, which counter skin irritations, are, for example, allantoin, bisabolol, dragosantol, camomile extract, panthenol, etc.

The cosmetic compositions according to the invention can comprise, as cosmetic and/or pharmaceutical active ingredient (and also optionally as auxiliary) at least one cosmetically or pharmaceutically acceptable polymer different from compounds of component A). These include, in very general terms, nonionic, anionic, cationic, amphoteric and neutral polymers. Preference is given to using water-soluble nonionic polymers.

Preferred polymers are nonionic, water-soluble or water-dispersible polymers or oligomers, such as polyethyleneimines and salts thereof, polyvinylamines and salts thereof, cellulose derivatives, polyvinylcaprolactam, e.g. Luviskol® Plus (BASF), or polyvinylpyrrolidone and copolymers thereof, in particular with vinyl esters, such as vinyl acetate and/or vinyl propionate, e.g. Luviskol® VA 37 (BASF); polyamides, e.g. based on itaconic acid and aliphatic diamines, as are described, for example, in DE-A-43 33 238. Preference is also given to homo- and copolymers of vinyl acetate as are described, for example, in U.S. Pat. No. 5,632,977.

Preferred polymers are also nonionic, siloxane-containing, water-soluble or -dispersible polymers, e.g. polyether siloxanes, such as Tegopren® (Goldschmidt) or Belsil® (Wacker).

Examples of anionic polymers are homo- and copolymers of acrylic acid and methacrylic acid or salts thereof, copolymers of acrylic acid and acrylamide and salts thereof; sodium salts of polyhydroxycarboxylic acids, polyaspartic acid and salts thereof, water-soluble or water-dispersible polyester, polyurethane and polyurea. Particularly suitable polymers are copolymers of t-butyl acrylate, ethyl acrylate, methacrylic acid (e.g. Luvimer® 100P), copolymers of ethyl acrylate and methacrylic acid (e.g. Luviumer® MAE), copolymers of N-tert-butylacrylamide, ethyl acrylate, acrylic acid (Ultrahold® 8, strong), copolymers of vinyl acetate, crotonic acid and optionally further vinyl esters (e.g. Luviset® grades), maleic anhydride copolymers, optionally reacted with alcohol, anionic polysiloxanes, e.g. carboxy-functional ones, t-butyl acrylate, methacrylic acid (e.g. Luviskol® VBM), copolymers of acrylic acid and methacrylic acid with hydrophobic monomers, such as, for example, $C_4$-$C_{30}$-alkyl esters of meth(acrylic acid), $C_4$-$C_{30}$-alkyl vinyl esters, $C_4$-$C_{30}$-alkyl vinyl ethers and hyaluronic acid. Examples of anionic polymers are also vinyl acetate/crotonic acid copolymers, as are commercially available, for example, under the names Resyn® (National Starch) and Gafset® (GAF) and vinylpyrrolidone/vinyl acrylate copolymers obtainable, for example, under the trade name Luviflex® (BASF). Further suitable polymers are the vinylpyrrolidone/acrylate terpolymer obtainable under the name Luviflex® VBM-35 (BASF) and sodium sulfonate-containing polyamides or sodium sulfonate-containing polyesters. Preference is also given to ethyl acrylate/methacrylic acid copolymers, such as, for example, Luviflex® Soft and methacrylic acid/tert-butyl acrylate graft copolymers based on polyalkylene oxide-containing silicone derivatives, such as, for example, Luviflex® Silk.

Further suitable polymers are cationic polymers with the name Polyquaternium according to INCI, e.g. copolymers of vinylpyrrolidone/N-vinylimidazolium salts (Luviquat® FC, Luviquat® HM, Luviquat® MS, Luviquat® Care), copolymers of N-vinylpyrrolidone/dimethylaminoethyl methacrylate, quaternized with diethyl sulfate (Luviquat® PQ 11), copolymers of N-vinylcaprolactam/N-vinylpyrrolidone/N-vinylimidazolium salts (Luviquat® Hold); cationic cellulose derivatives (polyquaternium-4 and -10), acrylamido copolymers (polyquaternium-7) and chitosan. Suitable cationic (quaternized) polymers are also Merquat® (polymer based on dimethyldiallylammonium chloride), Gafquat® (quaternary polymers which are formed by the reaction of polyvinylpyrrolidone with quaternary ammonium compounds), Polymer JR (hydroxyethylcellulose with cationic groups) and vegetable-based cationic polymers, e.g. guar polymers, such as the Jaguar® grades from Rhodia.

Suitable polymers are also amphoteric or zwitterionic polymers, such as the octylacrylamide/methyl methacrylate/tert-butylaminoethyl methacrylate/2-hydroxypropyl methacrylate copolymers obtainable under the names Amphomer® (National Starch), and also zwitterionic polymers, as are disclosed, for example, in German patent applications DE 39 29 973, DE 21 50 557, DE 28 17 369 and DE 37 08 451. Acrylamidopropyltrimethylammonium chloride/acrylic acid and methacrylic acid copolymers and alkali metal and ammonium salts thereof are preferred zwitterionic polymers. Further suitable zwitterionic polymers are methacroylethylbetaine/methacrylate copolymers which are commercially available under the name Amersette® (AMERCHOL), and copolymers of hydroxyethyl methacrylate, methyl methacrylate, N,N-dimethylaminoethyl methacrylate and acrylic acid (Jordapon®).

The formulation base of pharmaceutical compositions according to the invention preferably comprises pharmaceutically acceptable auxiliaries. Pharmaceutically acceptable auxiliaries are the auxiliaries which are known for use in the fields of pharmacy, food technology and related fields, in particular the auxiliaries listed in the relevant pharmacopeias (e.g. DAB Ph. Eur. BP NF), and other auxiliaries whose properties do not preclude a physiological application.

Suitable auxiliaries may be: lubricants, wetting agents, emulsifying and suspending agents, preservatives, antioxidants, antiirratative substances, chelating agents, emulsion stabilizers, film formers, gel formers, odor-masking agents, resins, hydrocolloids, solvents, solubility promoters, neutralizing agents, permeation accelerators, pigments, quaternary ammonium compounds, refatting and superfatting agents, ointment bases, cream bases or oil bases, silicone derivatives, stabilizers, sterilizing agents, propellants, drying agents, opacifiers, thickeners, waxes, softeners, white oils. Formulation in this regard is based on expert knowledge, as given, for example, in Fiedler, H. P. Lexikon der Hilfsstoffe für Pharmazie, Kosmetik und angrenzende Gebiete [Lexikon of auxiliaries for pharmacy, cosmetics and related fields], 4th ed., Aulendorf: ECV-Editio-Kantor-Verlag, 1996.

To prepare the dermatological compositions according to the invention, the active ingredients can be mixed or diluted with a suitable auxiliary (excipient). Excipients can be solid, semisolid or liquid materials which can also serve as vehicles, carriers or medium for the active ingredient. The admixing of further auxiliaries is carried out, where desired, in the manner known to the person skilled in the art.

According to a first preferred embodiment, the compositions according to the invention are a skin cleanser.

Preferred skin cleansers are soaps of liquid to gel-like consistency, such as transparent soaps, luxury soaps, deodorant soaps, cream soaps, baby soaps, skin protection soaps, abrasive soaps and syndets, pasty soaps, soft soaps and washing pastes, liquid washing, shower and bath preparations such as washing lotions, shower baths and shower gels, foam baths, oil baths and scrub preparations.

According to a further preferred embodiment, the compositions according to the invention are cosmetic compositions for the care and protection of the skin, nailcare compositions or preparations for decorative cosmetics.

Particular preference is given to skincare compositions, intimate care compositions, footcare compositions, light protection compositions, sunscreens, repellants, shaving compositions, depilatory compositions, antiacne compositions, make-up, mascara, lipsticks, eyeshadows, kohl pencils, eyeliners, blushers and eyebrow pencils.

The skincare compositions according to the invention are, in particular, W/O or O/W skin creams, day creams and night creams, eye creams, face creams, antiwrinkle creams, moisturizing creams, bleaching creams, vitamin creams, skin lotions, hair lotions and moisturizing lotions.

Skin cosmetic and dermatological compositions based on the above-described polymers A) exhibit advantageous effects. The polymers can, inter alia, contribute to the moisture retention and conditioning of the skin and to an improvement in the feel of the skin. The polymers can also act as thickeners in the formulations. By adding the polymers according to the invention, it is possible to achieve a considerable improvement in skin compatibility in certain formulations.

Skin cosmetic and dermatological compositions preferably comprise at least one copolymer A) in an amount of from about 0.001 to 50% by weight, preferably 0.01 to 30% by weight, very particularly preferably 0.1 to 20% by weight, based on the total weight of the composition.

Light protection agents based on the copolymers A), in particular, have the property of increasing the residence time of the UV-absorbing ingredients compared with customary auxiliaries such as polyvinylpyrrolidone.

Depending on the field of use, the compositions according to the invention can be applied in a form suitable for skincare, such as, for example as cream, foam, gel, pencil, mousse, milk, spray (pump spray or spray containing propellant) or lotion.

As well as comprising the polymers A) and suitable carriers, the skin cosmetic preparations can also comprise further active ingredients and auxiliaries customary in skin cosmetics and as described above. These include, preferably, emulsifiers, preservatives, perfume oils, cosmetic active ingredients, such as phytantriol, vitamin A, E and C, retinol, bisabolol, panthenol, light protection agents, bleaches, colorants, tinting agents, tanning agents, collagen, protein hydrolysates, stabilizers, pH regulators, dyes, salts, thickeners, gel formers, bodying agents, silicones, humectants, refatting agents and further customary additives.

Preferred oil and fatty components of the skin cosmetic and dermatological compositions are the abovementioned mineral and synthetic oils, such as, for example, paraffins, silicone oils and aliphatic hydrocarbons having more than 8 carbon atoms, animal and vegetable oils, such as, for example, sunflower oil, coconut oil, avocado oil, olive oil, lanolin, or waxes, fatty acids, fatty acid esters, such as, for example, triglycerides of $C_6$-$C_{30}$-fatty acids, wax esters, such as, for example, jojoba oil, fatty alcohols, vaseline, hydrogenated lanolin and acetylated lanolin, and mixtures thereof.

The polymers according to the invention can also be mixed with traditional polymers where specific properties are to be established.

The cosmetic or dermatological preparations are prepared by customary processes known to the person skilled in the art.

The cosmetic and dermatological compositions are preferably in the form of emulsions, in particular in the form of water-in-oil (W/O) or oil-in-water (O/w) emulsions. It is, however, also possible to choose other types of formulation, for example hydrodispersions, gels, oils, oleogels, multiple emulsions, for example in the form of W/O/W or O/W/O emulsions, anhydrous ointments or ointment bases, etc.

The emulsions are prepared by known methods. Apart from the copolymer A), the emulsions usually comprise customary constituents, such as fatty alcohols, fatty acid esters and, in particular, fatty acid triglycerides, fatty acids, lanolin and derivatives thereof, natural and synthetic oils or waxes and emulsifiers in the presence of water. The choice of emulsion type-specific additives and the preparation of suitable emulsions is described, for example, in Schrader, Grundlagen und Rezepturen der Kosmetika [Cosmetic bases and formulations], Hüthig Buch Verlag, Heidelberg, 2nd edition, 1989, third part, to which express reference is made here.

A suitable emulsion, e.g. for a skin cream, etc., generally comprises an aqueous phase which is emulsified by means of a suitable emulsifier system in an oil or fatty phase.

The proportion of the emulsifier systems in this type of emulsion is preferably about 4 to 35% by weight, based on the total weight of the emulsion. The proportion of the fatty phase is preferably about 20 to 60% by weight. The proportion of the aqueous phase is preferably about 20 to 70%, in each case based on the total weight of the emulsion. The emulsifiers are those customarily used in this type of emulsion. They are chosen, for example, from: $C_{12}$-$C_{18}$-sorbitan fatty acid esters; esters of hydroxystearic acid and $C_{12}$-$C_{30}$-fatty alcohols; mono- and diesters of $C_{12}$-$C_{18}$-fatty acids and glycerol or polyglycerol; condensates of ethylene oxide and propylene glycols; oxypropylenated/oxyethylated $C_{12}$-$C_{18}$-fatty alcohols; polycyclic alcohols, such as sterols; aliphatic alcohols with a high molecular weight, such as lanolin; mixtures of oxypropylenated/polyglycerolated alcohols and magnesium isostearate; succinic esters of polyoxyethylenated or polyoxypropylenated fatty alcohols; and mixtures of magnesium lanolate, calcium lanolate, lithium lanolate, zinc lanolate or aluminum lanolate and hydrogenated lanolin or lanolin alcohol.

Preferred fatty components which may be present in the fatty phase of the emulsions are: hydrocarbon oils, such as paraffin oil, purcellin oil, perhydrosqualene and solutions of microcrystalline waxes in these oils; animal or vegetable oils, such as sweet almond oil, avocado oil, calophylum oil, lanolin and derivatives thereof, castor oil, sesame oil, olive oil, jojoba oil, karite oil, hoplostethus oil; mineral oils whose distillation start-point under atmospheric pressure is at about 250° C. and whose distillation end-point is at 410° C., such as, for example, vaseline oil; esters of saturated or unsaturated fatty acids, such as alkyl myristates, e.g. i-propyl, butyl or cetyl myristate, hexadecylstearate, ethyl or i-propyl palmitate, octanoic or decanoic acid triglycerides and cetyl ricinoleate.

The fatty phase may also comprise silicone oils soluble in other oils, such as dimethylpolysiloxane, methylphenylpolysiloxane and the silicone glycol copolymer, fatty acids and fatty alcohols.

In order to favor the retention of oils, in addition to the polymers A), it is also possible to use waxes, such as, for example, carnauba wax, candililla wax, beeswax, microcrystalline wax, ozokerite wax and the oleates, myristates, linoleates and stearates of Ca, Mg and Al.

The water-in-oil emulsions are generally prepared by introducing the fatty phase and the emulsifier into a reaction vessel. The vessel is heated at a temperature of approximately 50 to 75° C., then the active ingredients and/or auxiliaries which are soluble in oil are added, and water which has been heated beforehand to approximately the same temperature and into which the water-soluble ingredients have optionally been dissolved beforehand is added with stirring. The mixture is stirred until an emulsion of the desired fineness is achieved, which is then left to cool to room temperature, if necessary with a lesser amount of stirring.

According to a further preferred embodiment, the compositions according to the invention are a shower gel, a shampoo formulation or a bath preparation.

Such formulations comprise at least one polymer A) and customary anionic surfactants as base surfactants and amphoteric and/or nonionic surfactants as cosurfactants. Further suitable active ingredients and/or auxiliaries are generally chosen from lipids, perfume oils, dyes, organic acids, preservatives and antioxidants, and thickener/gel formers, skin conditioning agents and humectants.

These formulations preferably comprise 2 to 50% by weight, preferably 5 to 40% by weight particularly preferably 8 to 30% by weight, of surfactants, based on the total weight of the formulation.

All anionic, neutral, amphoteric or cationic surfactants customarily used in body-cleansing compositions can be used in washing, shower and bath preparations.

Suitable anionic surfactants are, for example, alkyl sulfates, alkyl ether sulfates, alkylsulfonates, alkylarylsulfonates, alkyl succinates, alkyl sulfosuccinates, N-acylsarcosinates, acyl taurates, acyl isethionates, alkyl phosphates, alkyl ether phosphates, alkyl ether carboxylates, alpha-olefinsulfonates, in particular the alkali metal and alkaline earth metal salts, e.g. sodium, potassium, magnesium, calcium, and ammonium and triethanolamine salts. The alkyl ether sulfates, alkyl ether phosphates and alkyl ether carboxylates can have between 1 and 10 ethylene oxide or propylene oxide units, preferably 1 to 3 ethylene oxide units, in the molecule. These include, for example, sodium lauryl sulfate.

Suitable amphoteric surfactants are, for example, alkylbetaines, alkylamidopropylbetaines, alkylsulfobetaines, alkyl glycinates, alkyl carboxyglycinates, alkylamphoacetates or amphopropionates, alkyl amphodiacetates or amphodipropionates.

Suitable nonionic surfactants are, for example, the reaction products of aliphatic alcohols or alkylphenols having 6 to 20 carbon atoms in the alkyl chain, which may be linear or branched, with ethylene oxide and/or propylene oxide. The amount of alkylene oxide is about 6 to 60 mol per mole of alcohol. Also suitable are alkylamine oxides, mono- or dialkylalkanolamides, fatty acid esters of polyethylene glycols, ethoxylated fatty acid amides, alkyl polyglycosides or sorbitan ether esters.

The washing, shower and bath preparations can also comprise customary cationic surfactants such as, for example, quaternary ammonium compounds, for example cetyltrimethylammonium chloride.

In addition, it is also possible to use other customary cationic polymers, such as, for example, copolymers of acrylamide and dimethyldiallylammonium chloride (Polyquaternium-7), cationic cellulose derivatives (Polyquaternium-4, -10), guar hydroxypropyltrimethylammonium chloride (INCI: Hydroxylpropyl Guar Hydroxypropyltrimonium Chloride), copolymers of N-vinylpyrrolidone and quaternized N-vinylimidazole (Polyquaternium-16, -44, -46), copolymers of N-vinylpyrrolidone/dimethylaminoethyl methacrylate, quaternized with diethyl sulfate (Polyquaternium-11) and others.

The shower gel/shampoo formulations can further comprise thickeners, such as, for example sodium chloride, PEG-55, propylene glycol oleate, PEG-120 methyl glucose dioleate and others, and also preservatives, further active ingredients and auxiliaries and water.

In a further preferred embodiment the compositions according to the invention are hair-treatment compositions.

Hair-treatment compositions according to the invention preferably comprise at least one copolymer A) in an amount in the range from about 0.1 to 30% by weight, preferably 0.5 to 20% by weight, based on the total weight of the composition.

The hair-treatment compositions according to the invention are preferably in the form of a hair gel, setting foam, hair mousse, shampoo, hairspray or hair foam. Hairsprays include both aerosol sprays and also pump sprays without propellant gas. Hair foams include both aerosol foams and also pump foams without propellant gas.

Hairsprays and hair foams preferably comprise predominantly or exclusively water-soluble or water-dispersible components. If the compounds used in the hairsprays and hair foams according to the invention are water-dispersible, they can be used in the form of aqueous microdispersions with particle diameters of, usually, 1 to 350 nm, preferably 1 to 250 nm. The solids contents of these preparations are customarily in a range from about 0.5 to 20% by weight. These microdispersions generally do not require emulsifiers or surfactants for their stabilization.

Preferred hair-treatment compositions are in the form of an aqueous dispersion or in the form of an alcoholic or aqueous-alcoholic solution. Examples of suitable alcohols are ethanol, propanol, isopropanol and mixtures thereof.

Furthermore, the hair-treatment compositions according to the invention can generally comprise customary cosmetic auxiliaries, for example softeners, such as glycerol and glycol; emollients; perfumes; surfactants; UV absorbers; dyes; antistatic agents; agents for improving combability; preservatives; and antifoams.

If the compositions according to the invention are formulated as hairspray, they comprise a sufficient amount of a propellant, for example a low-boiling hydrocarbon or ether, such as propane, butane, isobutane or dimethyl ether. Propellants which can be used are also compressed gases, such as nitrogen, air or carbon dioxide. The amount of propellant here can be kept low in order not to increase the VOC content unnecessarily. This is then generally not more than 55% by weight, based on the total weight of the composition. If desired, however, higher VOC contents of 85% by weight and above are also possible.

The above-described polymers A) can also be used in combination with other hair polymers in the compositions. Suitable polymers are those described above.

The other hair polymers are preferably present in amounts up to 10% by weight, based on the total weight of the composition.

A preferred hair-treatment composition in the form of a gel comprises:

a) 0.1 to 20% by weight, preferably 1 to 10% by weight, of at least one polymer A), as defined above, b) 0 to 40% by weight of at least one carrier (solvent) chosen from $C_2$-$C_5$-alcohols, in particular ethanol, c) 0.01 to 5% by weight, preferably 0.2 to 3% by weight, of at least one thickener, d) 0 to 50% by weight of a propellant, e) 0 to 10% by weight, preferably 0.1 to 3% by weight, of at least one hair polymer which is different from a), preferably a water-soluble nonionic polymer, f) 0 to 1% by weight of at least one refatting agent, preferably chosen from glycerol and glycerol derivatives, g) 0 to 30% by weight of further active ingredients and/or auxiliaries, h) water ad 100% by weight.

A preferred hair-treatment composition in the form of a spray comprises:

a) 0.5 to 20% by weight, preferably 1 to 10% by weight, of at least one polymer A), as defined above, b) 50 to 99.5% by weight, preferably 55 to 99% by weight, of a carrier (solvent), chosen from water and water-miscible solvents, preferably $C_2$-$C_5$-alcohols, in particular ethanol, and mixtures thereof, c) 0 to 70% by weight, preferably 0.1 to 50% by weight, of a propellant, preferably chosen from dimethyl ether and alkanes, such as, for example, propane/butane mixtures,
d) 0 to 10% by weight, preferably 0.1 to 5% by weight, of at least one hair polymer which is different from a) preferably a water-soluble or -dispersible polymer,
e) 0 to 0,5% by weight, preferably 0.001 to 2% by weight, of at least one water-soluble or water-dispersible silicone compound, and optionally further active ingredients and/or auxiliaries, as defined above.

The composition according to the invention can comprise, as component e) at least one nonionic, siloxane-containing, water-soluble or -dispersible polymer, in particular chosen from the above-described polyethersiloxanes. The content of this component is then generally about 0.001 to 2% by weight, based on the total weight of the composition.

The invention is illustrated in more detail by reference to the following nonlimiting examples.

EXAMPLES

Example 1

Solution Polymerisation Method A

| Feed 1: | 400 g of vinylpyrrolidone |
| --- | --- |
|  | 400 g of vinylcaprolactam |
| Feed 2: | 75 g of methacrylic acid |
|  | 75 g of ethyl acrylate |
|  | 170 g of ethanol |
| Feed 3: | 15 g of Wako 50 (2,2'-azobis(2-amidinopropane)-dihydrochloride) |
|  | 135 g of water |
| Feed 4: | 10 g of Wako 50 (2,2'-azobis(2-amidinopropane)-dihydrochloride) |
|  | 90 g of water |

In a stirred apparatus with reflux condenser, internal thermometer and three separate feed devices, 80 g of feed 1, 15 g of feed 3 and 50 g of Mowiol® 4/88 (Polyvinyl alcohol, Hoechst) were introduced into 1 400 g of water, and the mixture was heated with stirring to about 60° C. Following the initial polymerization, recognizable from the viscosity starting to increase, at 60° C., the remainder of feed 1 was added over the course of 3 hours and the remainder of feed 3 over the course of 4 hours, during which the internal temperature was increased to about 65° C. When the addition was complete, the mixture was after-polymerized for a further 2 hours at this temperature. The viscous polymer solution was diluted by adding 600 g of ethanol. The aqueous-ethanolic solution was brought to a temperature of about 80° C. with stirring. Then, feed 2 was metered in over the course of 2 hours and feed 4 was metered in over the course of 3 hours and the mixture was polymerized. When the addition was complete, the mixture was after-polymerized for about 2 hours at a temperature of about 80° C. The solvent was removed by steam distillation. The resulting polymer solution was stirred at a temperature of 95 to 100° C. until the residual monomer content (vinylpyrrolidone and vinylcaprolactam) was <50 ppm (about 1 hour). This gave an approximately 30% strength aqueous dispersion. Pulverulent products can be obtained by spray-drying or freeze-drying.

All products were analogously polymerized with ethyl acrylate (examples No. 6 and 20).

Example 10

Solution Polymerization Method B

| Feed 1: | 300 g of vinylpyrrolidone |
| --- | --- |
|  | 300 g of vinylcaprolactam |
| Feed 2: | 20 g of methacrylic acid |
|  | 600 g of acrylamide (50% strength aqueous solution) |
|  | 30 g of dimethylaminoethyl methacrylate quaternized with dimethyl sulfate |
| Feed 3: | 15 g of Wako 50 (2,2'-azobis(2-amidinopropane)-dihydrochloride) |
|  | 135 g of water |
| Feed 4: | 10 g of Wako 50 (2,2'-azobis(2-amidinopropane)-dihydrochloride) |
|  | 90 g of water |

In a stirred apparatus with reflux condenser, internal thermometer and three separate feed devices, 60 g of feed 1, 15 g of feed 3 and 50 g of a water-soluble polyether urethane from polyethylene glycol and hexamethylene diisocyanate were initially introduced into 1 810 g of water, and the mixture was heated to 60° C. with stirring. After the initial polymerization, recognizable from the viscosity starting to increase, at 60° C., the remainder of feed 1 was added over the course of 3 hours and the remainder of feed 3 over the course of 4 hours, during which the internal temperature was increased to about 65° C. When the addition was complete, the mixture was after-polymerized for about a further 2 hours at this temperature. Feed 2 is then metered in over the course of 2 hours and feed 4 is metered in over the course of 3 hours and the mixture is polymerized at 60° C. When the addition is complete, the mixture was after-polymerized for a further about two hours at a temperature of about 80° C. The resulting polymer solution is stirred at a temperature of from 95 to 100° C. until the residual monomer content (vinylpyrrolidone and vinylcaprolactam) was <50 ppm (about 1 hour). This gave an approximately 30% strength aqueous pale yellow polymer solution.

Pulverulent products can be obtained by spray-drying or freeze-drying.

All products were polymerized analogously without ethyl acrylate (example Nos. 2-5 and 7-19).

TABLE 1

| Ex. No. | Initial charge | | Step 1 | | | | Step 2 | | | |
| --- | --- | --- | --- | --- | --- | --- | --- | --- | --- | --- |
| | PVOH | P(EU) | VP | VCap | AM | VFA | MAA 350- AM | | MA | EA | Q-DMAEMA |
| A | — | — | — | — | — | — | — | — | — | — |
| B | — | — | — | — | — | — | — | — | — | — |
| 1 | 5 | — | 40 | 40 | — | — | 7.5 | — | — | 7.5 | — |

TABLE 1-continued

| Ex. No. | Initial charge | | Step 1 | | | | Step 2 | | | | |
|---|---|---|---|---|---|---|---|---|---|---|---|
| | PVOH | P(EU) | VP | VCap | AM | VFA | MAA | AM | 350-MA | EA | Q-DMAEMA |
| 2  | 5  | 5 | 50 | —  | 30 | —  | 5   | 5  | —  | —  | —   |
| 3  | 10 | — | 50 | —  | —  | 30 | 5   | 5  | —  | —  | —   |
| 4  | —  | 7 | 50 | 30 | —  | —  | 4   | —  | —  | —  | 4   |
| 5  | —  | 5 | 40 | 30 | —  | —  | 3   | —  | 19 | —  | 3   |
| 6  | 5  | — | 30 | 30 | —  | —  | 10  | —  | 15 | 10 | —   |
| 7  | 5  | 5 | 40 | —  | 20 | —  | 5   | 25 | —  | —  | —   |
| 8  | 10 | — | 40 | —  | —  | 20 | 5   | —  | 25 | —  | —   |
| 9  | —  | 7 | 40 | 20 | —  | —  | 4   | 25 | —  | —  | 4   |
| 10 | —  | 5 | 30 | 30 | —  | —  | 2   | 30 | —  | —  | 3   |
| 11 | 10 | — | 30 | —  | —  | —  | 5   | —  | 50 | —  | 5   |
| 12 | 5  | 5 | 30 | 20 | —  | —  | 5   | 35 | —  | —  | —   |
| 13 | —  | 3 | 30 | 22 | —  | —  | 5   | —  | 40 | —  | —   |
| 14 | —  | 5 | 30 | 20 | —  | —  | 5   | 35 | —  | —  | 5   |
| 15 | —  | 5 | 30 | 30 | —  | —  | 2   | 30 | —  | —  | 3   |
| 16 | 10 | — | 30 | 20 | 30 | —  | 5   | 5  | —  | —  | —   |
| 17 | 5  | — | 30 | 20 | 30 | —  | 5   | 10 | —  | —  | —   |
| 18 | 5  | — | 25 | 25 | 30 | —  | 2.5 | —  | 10 | —  | 2.5 |
| 19 | —  | 5 | 30 | 20 | 35 | —  | 2.5 | —  | 5  | —  | 2.5 |
| 20 | —  | 5 | 30 | 20 | 35 | —  | 5   | —  | —  | 5  | 2.5 |

All data in parts by weight
PVOH: partially saponified polyvinyl alcohol (Mowiol ® 8-88, Clariant)
P(EU): polyether urethane from polyethylene glycol (Mn = 4000) and hexamethylene diisocyanate
VP: N-vinylpyrrolidone
VCap: N-vinylcaprolactam
AM: acrylamide
VFA: N-vinylformamide
MAA: methacrylic acid
AM: acrylamide
350-MA: Polyethylene glycol methacrylate (Mn = 350)
EA: ethyl acrylate
Q-DMAEMA: dimethylaminoethyl methacrylate-dimethyl sulfate Performance Properties
Standard Formulation:
0.3% by weight of a standard commercial polyacrylic acid thickener (Carbopol 940, BFGoodrich), neutralized with triethanolamine, is used to formulate a gel which, when applied to the hair, essentially shows no conditioning or setting action. The performance properties are given in table 2.

Comparative Examples A,B

3% by weight in each case of a standard commercial hair polymer (Ex. A: Polyvinylpyrrolidone, Ex. B: Vinylpyrrolidone-vinyl acetate copolymer) were added to the gel formulation from the standard formulation. The performance properties are shown in table 2. The products are still in need of improvement with regard to their stickiness.

In accordance with the invention:
3% by weight in each case of the copolymers 1 to 20 are added as hair cosmetic active ingredient to the gel formulation from the standard formulation. This gives clear formulations with good conditioning and setting action. The performance properties are likewise given in table 2.

Assessment:
A) Clarity

| Grade | Clarity |
|---|---|
| 1 | clear |
| 1-2 | almost clear |
| 2 | hand clear (clear when a thin film is formed on the hand) |
| 3 | slightly cloudy |
| 4 | cloudy |
| 5 | very cloudy |

B) Viscosity

| Grade | Viscosity |
|---|---|
| 1 | very solid |
| 1-2 | solid |
| 2 | moderately solid |
| 3 | flowing |

C) Stickiness

The stickiness was determined at a relative atmospheric humidity of 75% and at ambient temperature directly on dried films of the gel formulations.

| Grade | Stickiness |
|---|---|
| 1 | not sticky |
| 2 | slightly sticky |
| 3 | moderately sticky |
| 4 | sticky |
| 5 | very sticky |

TABLE 2

| Ex. No. | | Clarity | Viscosity | Stickiness |
|---|---|---|---|---|
| A | 3% Luviskol K90 + 0.3 Carbopol 940/TEA | 2 | 1-2 | 4 |
| B | 3% Luviskol VA64 + 0.3 Carbopol 940/TEA | 1-2 | 2 | 3 |
| 1 | 3% Polymer + 0.3 Carbopol 940/TEA | 1 | 1-2 | 1-2 |
| 2 | | 2 | 1-2 | 1-2 |
| 3 | | 2 | 1-2 | 2 |
| 4 | | 1-2 | 1 | 1-2 |
| 5 | | 1-2 | 1-2 | 2-3 |
| 6 | | 2 | 2 | 2 |
| 7 | | 2 | 1-2 | 1-2 |
| 8 | | 2-3 | 1-2 | 2 |
| 9 | | 1 | 1 | 1-2 |
| 10 | | 1-2 | 1-2 | 1-2 |
| 11 | | 1-2 | 2 | 1-2 |
| 12 | | 2 | 1-2 | 1 |
| 13 | | 2-3 | 1-2 | 1-2 |
| 14 | | 1-2 | 1 | 1-2 |
| 15 | | 1 | 1 | 1 |
| 16 | | 1-2 | 2 | 1 |
| 17 | | 1 | 1-2 | 1-2 |
| 18 | | 1 | 1-2 | 1 |
| 19 | | 1-2 | 1 | 1 |
| 20 | | 1-2 | 2 | 1 |

A) Hair gel:

Example Nos. 1-20

Hair Gel Containing Anionic Thickener:

| | [%] | CTFA |
|---|---|---|
| Phase 1: | | |
| Polymer 1-20 (30% strength aqueous solution) | 10.0 | |
| Glycerol | 0.2 | |
| D-Panthenol USP | 0.1 | Panthenol |
| Triethanolamine | 0.5 | |
| Water, dist. | 39.2 | |
| Additives, preservatives, soluble ethoxylated silicon, perfume | q.s. | |
| Phase 2: | | |
| Carbopol 940 (1% strength aqueous suspension) | 30.0 | Carbomer |
| Water, dist. | 20.0 | |

To prepare the hair gel, the components were weighed in and homogenized, stirring phase 2 into phase 1.

Examples Nos. 21-30

Hair Gel Containing a Further Setting Polymer and Thickener:

| | [%] | CTFA |
|---|---|---|
| Phase 1: | | |
| Polymer 1, 4, 5, 9, 10, 11, 17-20 (30% strength aqueous solution) | 7.0 | |
| Luviskol VA 64 | 1.0 | Vinylpyrrolidone-vinyl acetate copolymer |
| Uvinul MS 40 | 0.2 | Benzophenone-4 |
| Glycerol | 0.2 | |
| D-Panthenol USP | 0.1 | Panthenol |
| Triethanolamine | 0.5 | |
| Ethanol | 10.0 | |
| Water, dist. | 31.0 | |
| Additives, preservatives, soluble ethoxylated silicon, perfume | q.s. | |
| Phase 2: | | |
| Carbopol 940 (1% strength aqueous suspension) | 30.0 | Carbomer |
| Water, dist. | 20.0 | |

To prepare the hair gel, the components were weighed in and homogenized, stirring phase 2 into phase 1.

B) Setting Foam:

Example Nos. 31-40

| Foam conditioner: | [%] |
|---|---|
| Polymer 1-4, 15-20 (30% strength aqueous solution) | 15.0 |
| Cremophor A 25 (Ceteareth 25/BASF) | 0.2 |
| Comperlan KD (Coamide DEA/Henkel) | 0.1 |
| Water | 74.7 |
| Dimethyl ether | 10.0 |
| Additives, preservatives, perfume | q.s. |

To prepare the foam conditioner, the components were weighed in and dissolved with stirring. They are then filled into a dispenser and the propellant gas is added.

C) Hair Spray:

Example Nos. 41-50

| VOC 80 Aerosol hair spray | [%] |
|---|---|
| Polymer No. 1, 6, 9, 10, 12-15, 19, 20 (30% strength aqueous solution) | 5.0 |
| Luviset PUR | 1.50 |
| Water | 13.50 |
| Dimethyl ether | 40.00 |
| Ethanol | 40.00 |
| Additives, silicone, perfume, defoamer | q.s. |

Example Nos. 51-60

| VOC 55 Aerosol hair spray | [%] |
|---|---|
| Polymer No. 1, 6, 9, 10, 12-15, 19, 20 (30% strength aqueous solution) | 7.0 |
| Luviset PUR | 1.00 |
| Water | 37.00 |
| Dimethyl ether | 35.00 |
| Ethanol | 20.00 |
| Additives, silicone, perfume, defoamer | q.s. |

Example Nos. 61-70

| VOC 55 Hand pump spray | [%] |
|---|---|
| Polymer No. 1, 6, 9, 10, 12-15, 19, 20 (30% strength aqueous solution) | 10.0 |
| Water | 35.00 |
| Ethanol | 55.00 |
| Additives, silicone, perfume, defoamer | q.s. |

D) Shampoo:

Example Nos. 71-80

| | Conditioner Shampoo: | [%] |
|---|---|---|
| A) | Texapon NSO 28% strength (Sodium Laureth Sulphate/Henkel) | 50.0 |
| | Comperlan KD (Coamide DEA/Henkel) | 1.0 |
| | Polymer No. 4, 5, 9-11, 14, 15, 18-20 (30% strength aqueous solution) | 3.0 |
| | Water | 17.0 |
| | Perfume oil | q.s. |
| B) | Water | 27.5 |
| | Sodium chloride | 1.5 |
| | Preservative | q.s. |

To prepare the shampoo, the components of the respective phases A) and B) are weighed in and homogenized with stirring. Phase B) is then slowly stirred into phase A).

Use in Skin Cosmetics:

Example Nos. 81-100

| Standard O/W cream: | | |
|---|---|---|
| | [%] | CTFA Name |
| Oil phase: | | |
| Cremophor A6 | 3.5 | Ceteareth-6 (and) Stearyl Alcohol |
| Cremophor A25 | 3.5 | Ceteareth-25 |
| Glycerol monostearate s.e. | 2.5 | Glyceryl Stearate |
| Paraffin oil | 7.5 | Paraffin Oil |
| Cetyl alcohol | 2.5 | Cetyl Alcohol |
| Luvitol EHO | 3.2 | Cetearyl Octanoate |
| Vitamin E acetate | 1.0 | Tocopheryl Acetate |
| Nip-Nip | 0.1 | Methyl and Propyl 4-hydroxybenzoates (7:3) |
| Water Phase: | | |
| Polymer No. 1-20 (30% strength aqueous solution) | 3.0 | |
| Water | 74.6 | Water |
| 1,2-Propylene glycol | 1.5 | Propylene Glycol |
| Germall II | 0.1 | Imidazolidinyl-Urea |

To prepare the cream, the components of the oil phase and of the water phase were in each case weighed in separately and homogenized at a temperature of 80° C. with stirring. The water phase is then slowly stirred into the oil phase. The mixture is then left to slowly cool to room temperature with stirring.

Example Nos. 101-120

| Day lotion: | | |
|---|---|---|
| | [%] | CTFA Name |
| Oil phase: | | |
| Cremophor A6 | 1.5 | Ceteareth-6 (and) Stearyl Alcohol |
| Cremophor A25 | 1.5 | Ceteareth-25 |
| Glycerol monostearate s.e. | 5.0 | Glyceryl Stearate |
| Uvinul MS 40 | 0.5 | Benzophenone-4 |
| Paraffin oil | 3.5 | Paraffin Oil |
| Cetyl alcohol | 0.5 | Cetyl Alcohol |
| Luvitol EHO | 10.0 | Cetearyl Octanoate |
| D-Panthenol 50 P | 3.0 | Panthenol and Propylene glycol |
| Vitamin E acetate | 1.0 | Tocopheryl Acetate |
| Tegiloxan 100 | 0.3 | Dimethicone |
| Nip-Nip | 0.1 | Methyl and Propyl 4-hydroxybenzoates (7:3) |
| Water Phase: | | |
| Polymer No. 1-20 (30% strength aqueous solution) | 1.5 | |
| Water | 70.0 | Water |
| 1,2-Propylene glycol | 1.5 | Propylene Glycol |
| Germall II | 0.1 | Imidazolidinyl-Urea |

To prepare the cream, the components of the oil phase and of the water phase are in each case weighed in separately and homogenized at a temperature of 80° C. with stirring. The water phase is then slowly stirred into the oil phase. The mixture is then left to slowly cool to room temperature with stirring.

We claim:

1. A cosmetic or pharmaceutical composition comprising, in a cosmetically acceptable carrier, at least one water-soluble or water-dispersible copolymer A), which does not comprise any groups comprising a silicon atom and which is obtained by two-stage free-radical copolymerization of a monomer mixture of component
   a) 20 to 99.9% by weight of at least one N-vinyllactam,
   b) 0.1 to 30% by weight of at least one compound with a free-radically polymerizable, α,β-ethylenically unsaturated double bond and at least one anionogenic group per molecule,
   c) 0.1 to 65% by weight of at least one free-radically polymerizable compound selected from component
      c1) open-chain, α,β-ethylenically unsaturated compounds of the formula I

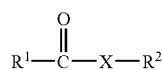

(I)

wherein
   one of the radicals $R^1$ or $R^2$ is a group of the formula $CH_2=CR^3—$ wherein $R^3=H$ or $C_1$-$C_4$-alkyl and the other radical is H, alkyl, hydroxyalkyl, aminoalkyl, the N-alkyl and N,N-dialkyl derivatives thereof or a polyether radical comprising at least 5 alkylene oxide units, and X is O or NR$^4$, wherein R$^4$ is hydrogen, C$_1$-C$_7$-alkyl or a polyether radical comprising at least 5 alkylene oxide units, c2) compounds with a free-radically polymerizable, α,β-ethylenically unsaturated double bond and at least one anionic or cationic group per molecule, d) 0 to 15% by weight of at least one copolymerizable monomer which is different from a) to c)

wherein the weight percentage of components a), b), c) and d) are based on the total weight of components a) to d), and wherein components b) and c) are different, in the presence of at least one water-soluble component e) which does not contain any carbon-carbon double bonds and which comprises at least one polyether urethane, wherein said two-stage free-radical copolymerization comprises:

i) polymerizing all of component a) and an amount of from 0 up to and including all of component c) in the presence of at least a portion of one of component e) to give a first polymer A1), and ii) adding and polymerizing, to polymer A1) obtained in i), all of component b) and component d) and if remaining from i) the component c) and component e) to give the copolymer A).

2. A composition as claimed in claim 1, wherein component c) comprises at least one compound selected from the group consisting of N-vinylamides of saturated monocarboxylic acids, amides of α,β-ethylenically unsaturated monocarboxylic acids and their N-alkyl, N-polyalkylene glycol, N,N-dialkyl, aminoalkyl, (N-alkylamino)alkyl, (N,N-dialkylamino)alkyl and N,N-di(polyalkenylene glycol) derivatives, alkyl(meth)acrylates, polyether acrylates and mixtures thereof.

3. A composition as claimed in claim 1 wherein the copolymer A) is obtained by free-radical copolymerization of
20 to 90% by weight of at least one N-vinyllactam of component a),
1 to 20% by weight of at least one component b) and
5 to 65% by weight of at least one component c)
in the presence of at least one component e).

4. A composition as claimed in claim 3, wherein
component a) is N-vinylpyrrolidone and/or N-vinylcaprolactam,
component b) is (meth)acrylic acid, and
component c) is selected from the group consisting of N-vinylamides of saturated monocarboxylic acids, amides of α,β-ethylenically unsaturated monocarboxylic acids, N, N-dialkylaminoalkyl (meth)acrylates, C$_1$-C$_3$-alkyl (meth)acrylates, polyalkylene glycol (meth)acrylates and mixtures thereof.

5. A composition as claimed in claim 1, wherein the cosmetically acceptable carrier is selected from the group consisting of i) water,
ii) water-miscible organic solvents,
iii) propellant gases,
iv) oils, fats, waxes,
v) esters of C$_6$-C$_{30}$-monocarboxylic acids with mono-, di- or trihydric alcohols which are different from iv),
vi) saturated acyclic and cyclic hydrocarbons,
vii) fatty acids,
viii) fatty alcohols
and mixtures thereof.

6. A composition as claimed in claim 1, wherein said composition is in the form of a gel, foam, spray, an ointment, cream, emulsion, suspension, lotion, milk or paste.

7. A composition as claimed in claim 1, wherein the polymerization in step i) takes place in water and the polymerization in step ii) takes place in a water/C$_1$-C$_4$-alkanol mixture.

8. A composition as claimed in claim 1, wherein the polymerization in step i) takes place at a pH of ≧6.5 and the polymerization in step ii) takes place at a pH of <6.5.

9. A copolymer A) as claimed in claim 1.

10. A method of cleansing, caring and/or protecting skin which comprises:
preparing a skin cleansing composition, skin care composition, and/or skin protecting composition comprising the composition as claimed in claim 1, and
applying the skin cleansing composition, skin care composition, and/or skin protecting composition to the skin.

11. A method of treating hair, which comprises
preparing a hair treatment composition comprising the composition as claimed in claim 1, and
applying the hair treatment composition to hair.

12. The method of treating hair as claimed in claim 11, wherein the hair treatment composition is applied to the hair as setting agents and/or as conditioners.

13. The method of treating hair as claimed in claim 12, wherein the hair treatment composition is in the form of a hair gel, shampoo, setting foam, hair tonic, hairspray or hair foam.

14. A finger or toe nail treatment method, which comprises:
preparing a nail care composition comprising the composition as claimed in claim 1, and
applying the nail care composition to at least one finger or toe nail.

15. A method of applying preparations for decorative cosmetics which comprises,
preparing a decorative cosmetic preparation comprising the composition as claimed in claim 1, and
applying the decorative cosmetic preparation to areas to be cosmetically decorated.

16. A copolymer A) as claimed in claim 4.

17. The composition as claimed in claim 5, wherein the carrier comprises a water-miscible organic solvent, which is a C$_1$-C$_4$-alkanol.

* * * * *